(12) United States Patent
Sauer (10) Patent No.: US 8,398,657 B2
(45) Date of Patent: Mar. 19, 2013

(54) MULTI-FIRE SUTURING INSTRUMENT WITH PROXIMAL FERRULE RELEASE FEATURE

(75) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 633 days.

(21) Appl. No.: 12/622,173

(22) Filed: Nov. 19, 2009

(65) Prior Publication Data

US 2011/0118758 A1    May 19, 2011

(51) Int. Cl.
*A61B 17/04* (2006.01)
(52) U.S. Cl. ....................................................... 606/144
(58) Field of Classification Search ........................ None
See application file for complete search history.

(56) References Cited

U.S. PATENT DOCUMENTS

| | | | | |
|---|---|---|---|---|
| 3,168,097 A | * | 2/1965 | Dormia | 606/147 |
| 5,235,966 A | * | 8/1993 | Jamner | 600/204 |
| 5,290,308 A | * | 3/1994 | Knight et al. | 606/205 |
| 5,507,756 A | * | 4/1996 | Hasson | 606/139 |
| 5,520,702 A | * | 5/1996 | Sauer et al. | 606/144 |
| 5,575,805 A | * | 11/1996 | Li | 606/206 |
| 6,146,392 A | * | 11/2000 | Smith | 606/147 |
| 6,533,796 B1 | * | 3/2003 | Sauer et al. | 606/144 |
| 2002/0123756 A1 | * | 9/2002 | Sauer | 606/139 |
| 2004/0015177 A1 | | 1/2004 | Chu | |
| 2004/0116855 A1 | * | 6/2004 | Popov et al. | 604/110 |
| 2005/0154403 A1 | | 7/2005 | Sauer et al. | |

FOREIGN PATENT DOCUMENTS

WO     0224078 A    3/2002

OTHER PUBLICATIONS

United Kingdom Intellectual Property Office—Search Report Under Section 17 Dated Nov. 23, 2010, 1 page.

* cited by examiner

*Primary Examiner* — Melanie Tyson
*Assistant Examiner* — Son Dang
(74) *Attorney, Agent, or Firm* — Stephen B. Salai, Esq.; Harter Secrest & Emery LLP (57) ABSTRACT

A surgical suturing instrument has a needle which traverses at tissue receiving gap and picks up suture distal to the gap. This invention provides an automated mechanism enabling the suture to be removed from the needle after the needle is retracted proximal to the tissue gap. This mechanism provides enhanced device reloading and other potential uses.

15 Claims, 10 Drawing Sheets

MULTI-FIRE SUTURING INSTRUMENT WITH PROXIMAL FERRULE RELEASE FEATURE

CROSS-REFERENCE TO RELATED APPLICATIONS

None.

STATEMENT REGARDING FEDERALLY SPONSORED RESEARCH OR DEVELOPMENT

None

NAMES OF THE PARTIES TO A JOINT RESEARCH AGREEMENT

None

REFERENCE TO A "SEQUENCE LISTING"

None

BACKGROUND OF THE INVENTION

1. Field of the Invention

This invention relates generally to surgical suturing instruments and more particularly to a surgical suturing instrument of the type in which a reciprocating needle picks up a ferrule at the end of a suture, from a magazine disposed at a distal end of the instrument and pulls the ferrule and associated suture back across a gap. The invention also provides a stripper for detaching the ferrule from the needle at the proximal end of the gap.

2. Description of Related Art

Surgical suturing instruments that use a reciprocating needle for penetrating a tissue segment, picking up a suture by attaching to a ferrule attached to the end of the suture and pulling the suture back through the tissue are known. Recently, improved instruments of this type as shown, for example, in U.S. Pub. No. 2005/0154403 have been developed that include a mechanism for detaching the ferrule from the needle at the distal end of the instrument. These instruments have enabled an expanded variety of stitches to be placed.

To enable an even greater variety of stitches to be placed by the instrument, there is a further need, for a surgical suturing instrument that can provide multiple sutures and in which ferrules can be detached from the needle at the proximal end of the gap. Heretofore, a couple of manual techniques have been used to remove ferrules from needles proximal to the tissue gap; namely, physically pulling the ferrule from the tip of the needle by grasping and tensioning the suture, and grasping the ferrule itself, often with a needle driver or surgical clamp to physically remove it from the end of the needle. While each of these is effective, each requires access to the suture or the ferrule, respectively, and therefore requires that the instrument be withdrawn from the site where the sutures are being placed. With the ferrule and suture removal from the needle more automated through one aspect of this invention, another aspect of this invention, multiple suture loads in the device, offers an improved opportunity to expedite suturing. This proximal ferrule release mechanism is useful in unloading the ferrules from the needle prior to reloading the device inside or outside of the patient.

BRIEF SUMMARY OF THE INVENTION

The instruments to which this invention is addressed offer many novel features that improve a surgeon's ability to place multiple suture bites for suture placement during minimally invasive surgery. Since more automated ferrule release helps enable multi-fire devices, the proximal ferrule release will be addressed first. This new ferrule release enhancement addresses the need to mechanically remove the ferrule from the needle on the proximal side of the gap. Previously, ferrules required mechanical removal from needles retracted into the proximal jaw by pulling the suture attached to the ferrule away from the needle or using a clamp to directly pull the ferrule off. This new more automated mechanical ferrule release mechanism assists in the instrument reloading process and may be used in future devices as alternative means of multiple suture placement.

It is an object of this invention to provide a surgical suturing instrument that can separate the ferrule from the needle at the proximal side of the gap without withdrawing the instrument from the suturing site.

Briefly stated and in accordance with one aspect of this invention, a surgical suturing instrument includes a housing having a handle and an actuating member, an elongated guide member attached to the housing and having a distal end, a tip having a tissue engaging gap disposed the distal end of the elongated guide member, and a needle extending from the housing through the guide member, across the gap, to the distal end of the tip, the needle reciprocally movable across the gap from a proximal end of the gap to the distal end of the gap by movement of the actuating member from a rest position to a retracted position and movable proximally from the proximal end of the gap into the guide member by movement of the actuating member from the rest position to an extended position in a direction opposite the retracted position.

In accordance with another aspect of this invention, the surgical suturing instrument includes a ferrule stripper engaging the needle for removing the ferrule from attachment with the needle as the actuating member is moved from the rest position to the extended position.

In accordance with another aspect of the invention, the ferrule stripper comprises a resilient member having a ferrule engaging portion riding on the needle proximal to the needle tip.

In accordance with another aspect of the invention, the needle has a flat surface adjacent the tip of the needle exposing a proximal edge of the ferrule when the ferrule is attached to the needle and in which the stripper engages the proximal edge of the ferrule to remove the ferrule from the tip of the needle.

In accordance with another aspect of the invention, the actuating member is pivotally mounted on the housing.

In accordance with another aspect of the invention, a first spring biases the actuating member from the retracted position to the rest position.

In accordance with another aspect of the invention, a second spring biases the actuating member from the extended position to the rest position.

In another aspect of the invention a spring biases the handle from the retracted position to the extended position and a latch stops the handle at the rest position until the latch is released. Further movement of the slidable latch aids in retracting the needle to strip the ferrule.

In accordance with another aspect of this invention, multiple ferrules with sutures are located in a magazine at the distal end of the device to enable multiple suture placements without reloading more sutures into the device tip. Springs or other mechanisms can be used to reposition subsequent ferrules in line with the needle for pick-up. Single ferrules on single sutures or two ferrules on opposite ends of the single suture or various combinations could be deployed.

In accordance with another aspect of the invention, the housing comprises a handle that can be gripped and the actuating member operated with one hand.

While the novel aspects of the invention are set forth with particularity in the appended claims, the invention itself together with further objects and advantages thereof may be more readily understood by reference to the following detailed description of several embodiments of the invention taken in connection with the accompanying drawings.

DETAILED DESCRIPTION OF THE INVENTION

Figure 1:
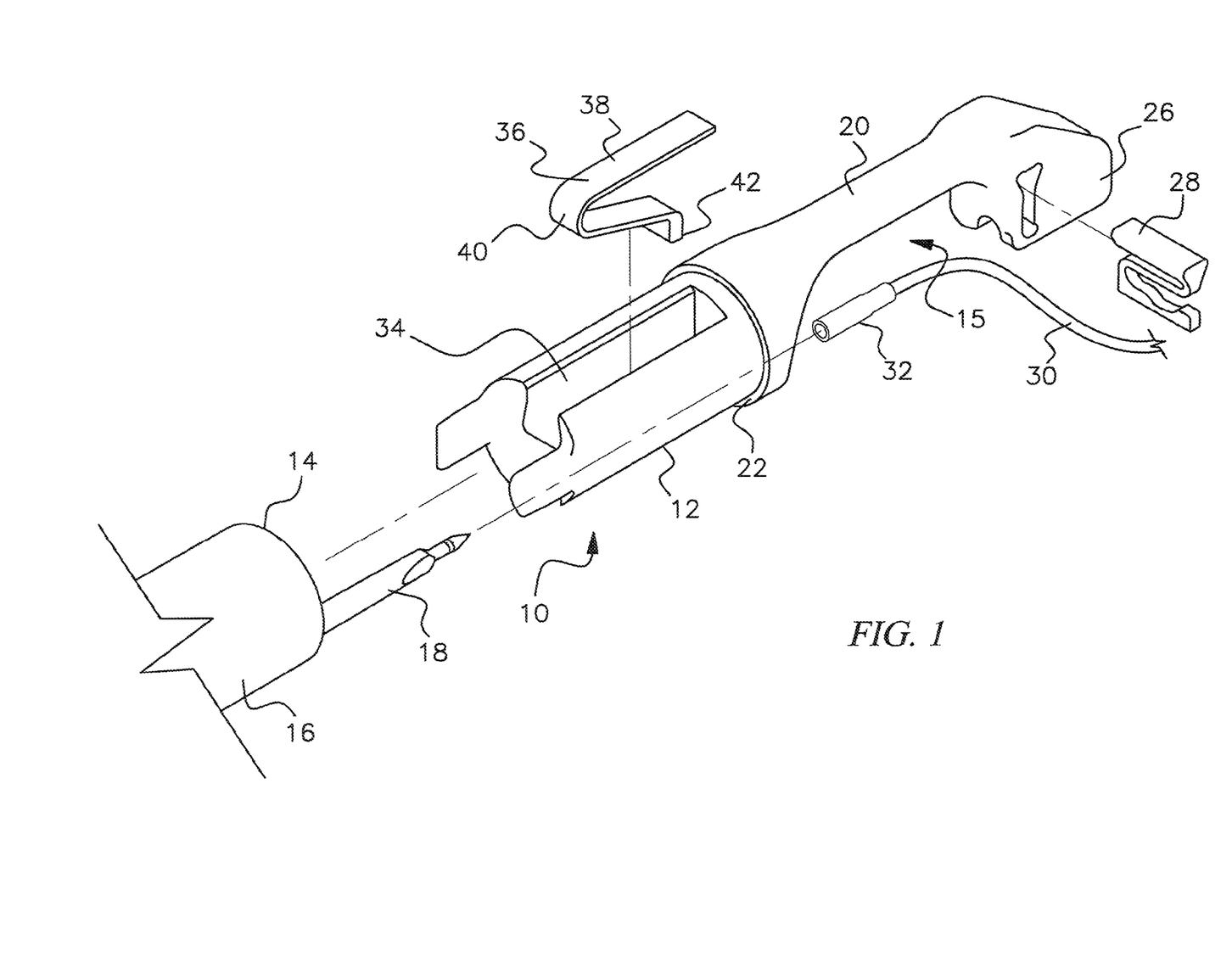
FIG. 1 is an exploded view of the tip of a surgical suturing instrument in accordance with this invention showing the components thereof.

FIG. 1 is an exploded enlarged view of the tip 10 of the surgical suturing instrument in accordance with this invention. The tip 10 which may be a machined or molded piece has a preferably cylindrical proximal portion 12 that fits within the distal end of a shaft tube 16 carrying a needle 18. The proximal portion 12 of the tip 10 has a diameter adapted to fit within the inside diameter of the shaft tube 16, and a distal portion 20 has a larger diameter terminating in a proximal shoulder 22 that abuts the distal end 14 of the shaft tube 16. The distal portion 20 includes a tissue receiving gap 15 and terminates in a suture/ferrule receiving tip 26 having a latch 28 disposed therein for holding a suture 30 with attached ferrule 32 for pickup by a needle in a manner well known to those skilled in the art.

The proximal portion 12 includes a cavity 34 for receiving a ferrule stripping spring 36. The spring 36 has an elongated flat portion, a bend 40, and a slightly shorter needle engaging portion terminating in a lip 42. The ferrule stripping spring 36 is resiliently deformable by bringing the two legs of its generally v-shape together. The spring 36 fits within the cavity 34 with the long portion 38 up, and the lip 42 exposed in a recess in the proximal portion of the tip 10.

The operation of the ferrule stripping spring 36 will be described in more detail below.

Figure 2:
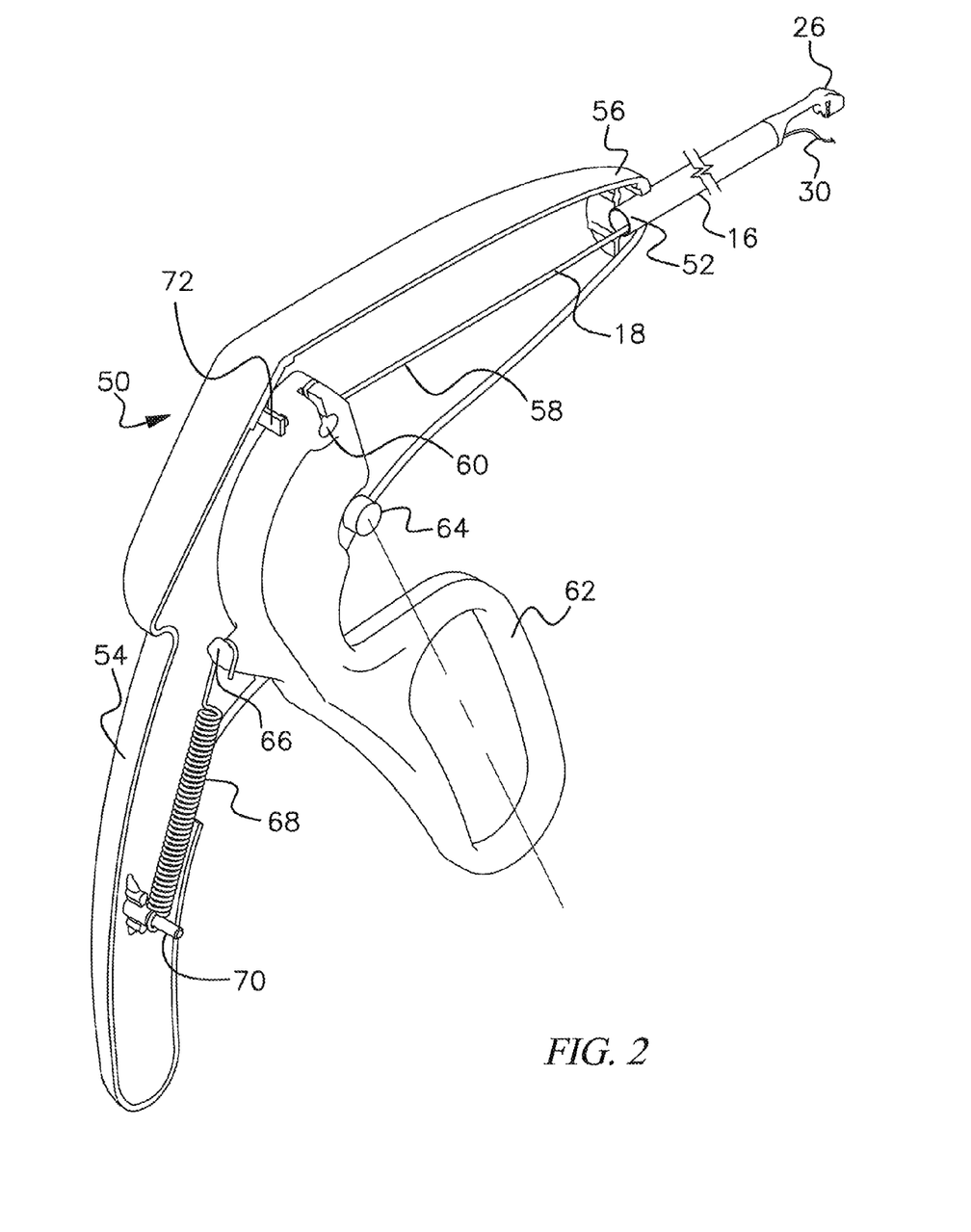
FIG. 2 is a cutaway perspective view of a surgical suturing instrument in accordance with this invention with an actuating lever in the rest position.

FIG. 2 is a cutaway isometric view of a surgical suturing instrument 50 in accordance with this invention. The shaft tube 16 and distal tip 26 illustrated in FIG. 1 appear. The proximal portion 52 of the shaft tube 16 is engaged with the tip 56 of a grippable handle 54 through which the proximal end 58 of the reciprocating needle 18 is passed to an upper needle end receiving portion 60 of an operating lever 62 pivotally mounted in the handle 54 at a lever pivot point 64. Preferably, the proximal end 58 of the needle 18 has an enlarged head, not visible, received in a cavity 60 in the upper end of the operating lever 62. The operating lever includes a spring attachment projection 66 on which one end of a retracting spring 68 is engaged, the opposite end of the spring 68 being fixed to a post 70 in the lower portion of the handle 54. The retraction spring 68 urges the operating lever 62 from a retracted position to a rest position that is, with the operating lever 62 extended so that the needle 18 is retracted to the proximal end of the gap. A flexible stop 72 is mounted to the handle and engages the upper portion of the operating lever 62 to restrain further extension of the lever. The flexible stop exerts force on the lever that can be overcome by further manual movement of the lever 62 to an extended position in a direction away from the handle 54 such as by gripping the lever and pulling on it. The further movement of the lever 62 further retracts the needle 18 into the proximal portion of the tip to strip off the ferrule 32 in a manner that will be discussed below.

Figure 3:
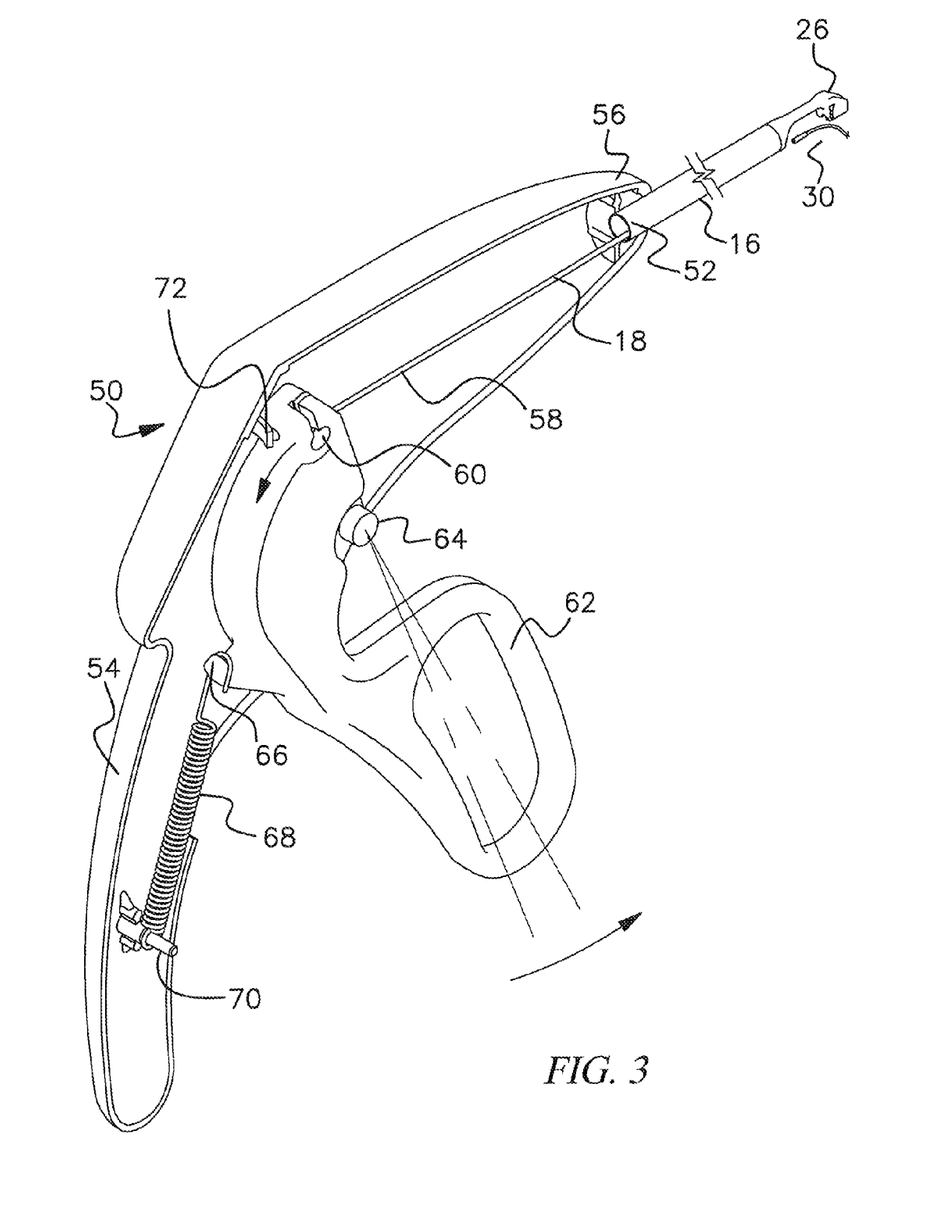
FIG. 3 is a cutaway perspective view of a surgical suturing instrument in accordance with this invention with an actuating lever in an extended position.

FIG. 3 shows the instrument of FIG. 2 with the operating lever 62 moved to the full forward extended position fully retracting the needle 18 against the bias of the flexible stop 72 which is shown now bent to accommodate full needle retraction.

Figure 4:
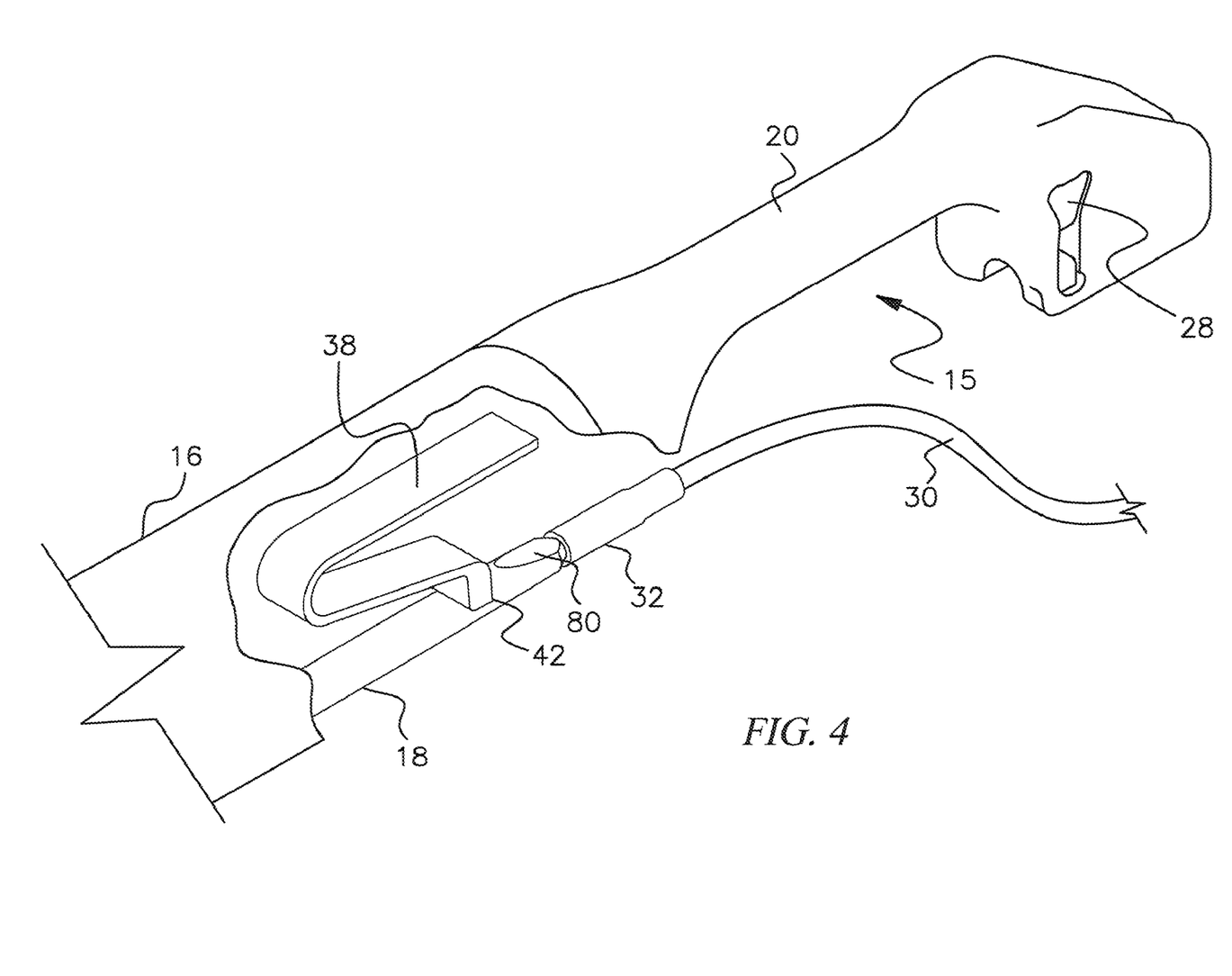
FIG. 4 is an enlarged view of the tip of the instrument with a portion thereof cut away showing the relationship of the ferrule stripper to the needle at the resting position.

FIG. 4 is an enlarged view of the distal end of the surgical suturing instrument 50 showing the elements thereof in the rest position, that is, with the needle 18 retracted to the proximal end of the gap 15 but not pulled back against the resilient stop. As can be seen, the flexible ferrule stripping spring 42 lip engages the shaft of the needle 18 proximal to the ferrule engaging tip. A flat spot 80 is formed on the needle shaft between the point at which the spring lip engages the needle 18 and the proximal end of the ferrule 34 for facilitating stripping of the ferrule from the needle as will be shown below.

Figure 5:
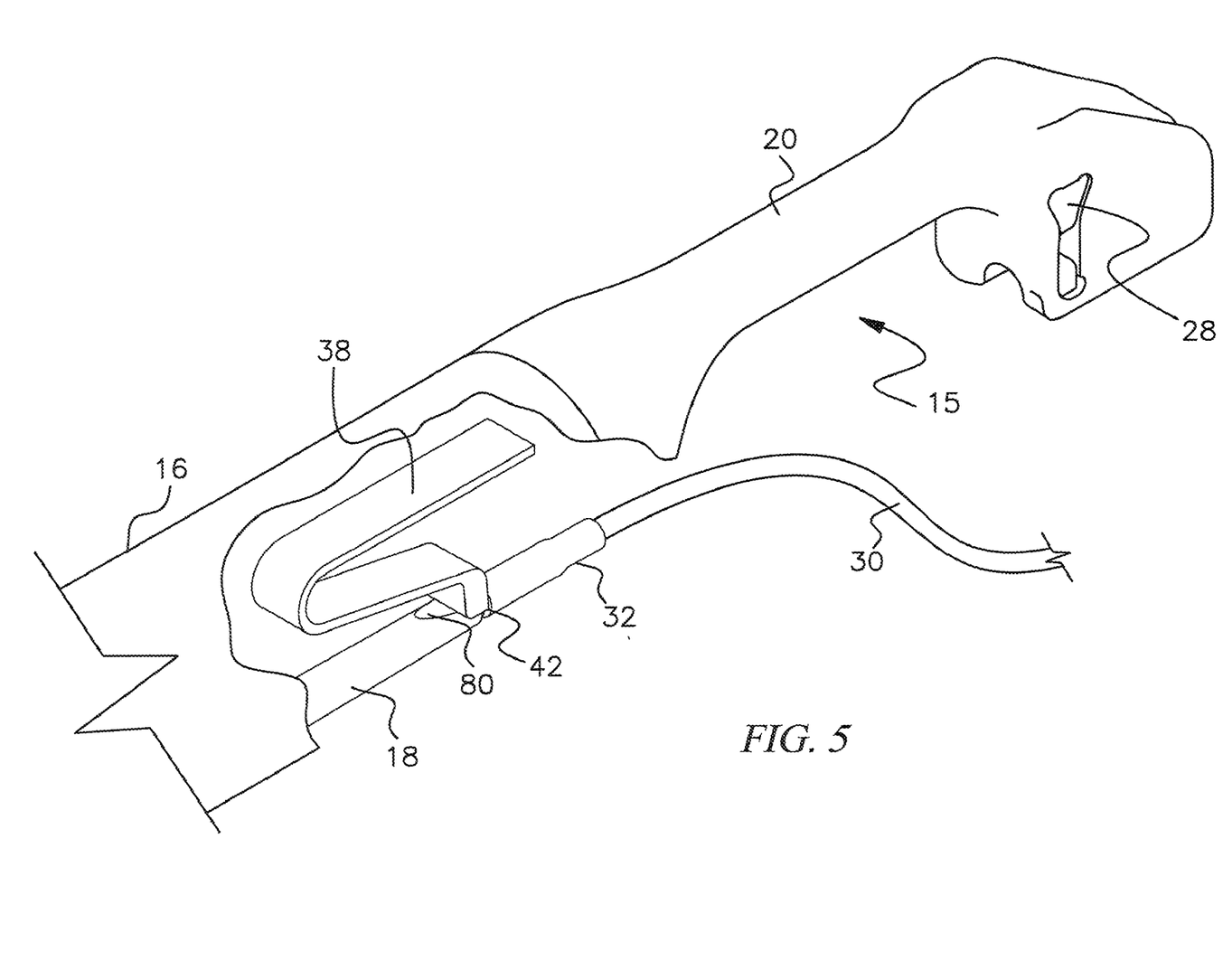
FIG. 5 is a view similar to FIG. 4 showing the ferrule stripper engaging the ferrule.

FIG. 5 shows the distal end of the surgical suturing instrument as the needle 18 is drawn back from the rest position shown in FIG. 4 towards the fully retracted ferrule stripping position. It can be seen that the ferrule engaging lip 42 of the resilient spring 36 engages the flat 80 on the shaft of the needle 18 so that the distal end of the spring lip engages the proximal end of the ferrule 32.

Figure 6:
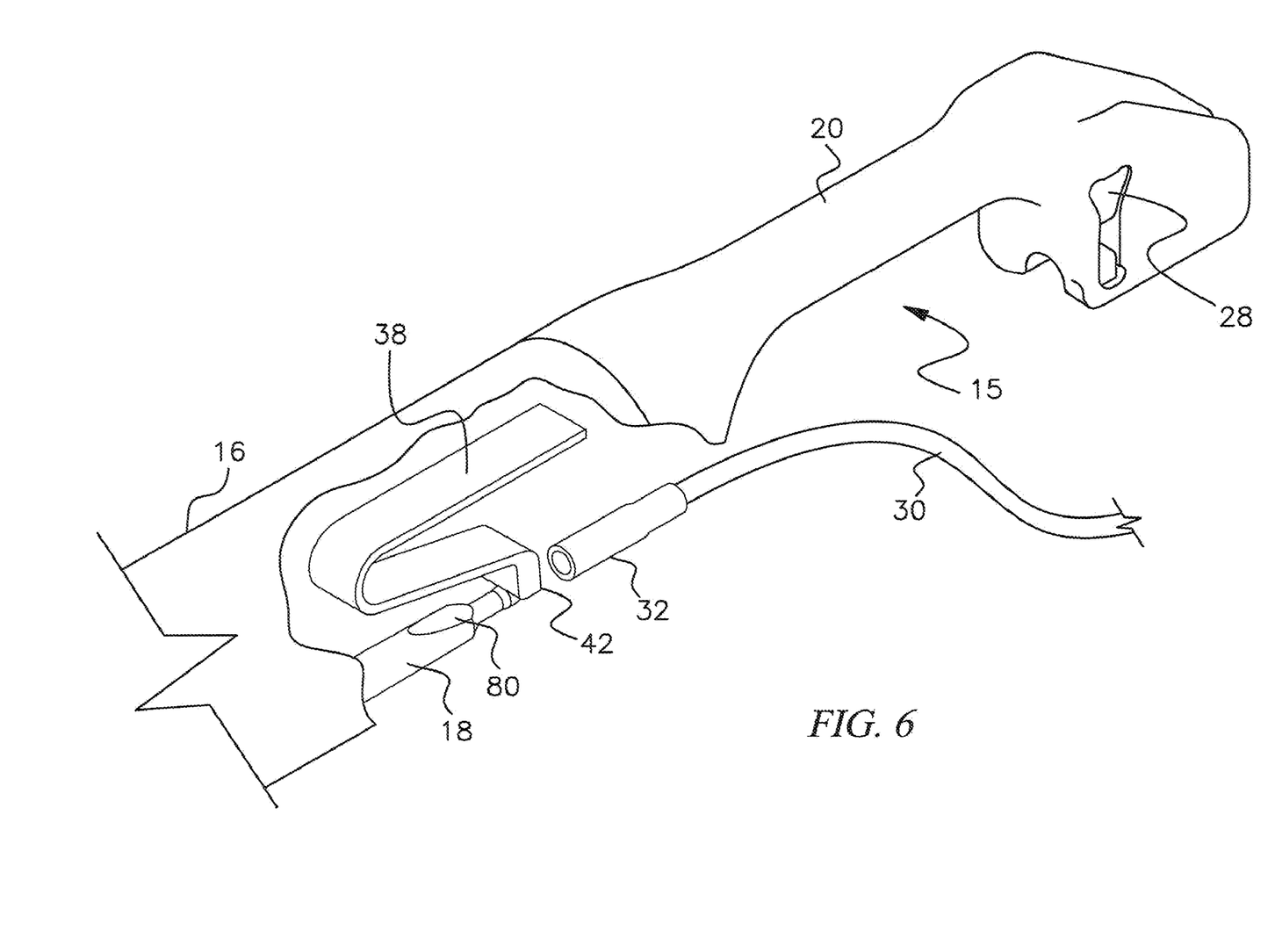
FIG. 6 is a view similar to FIGS. 4 and 5 showing the ferrule detached from the tip of the needle, which is fully retracted.

As shown in FIG. 6, as the needle is retracted further against the resilient stop, the needle engaging lip 42 of the spring 36 pushes the ferrule off the end of the needle.

Figure 7:
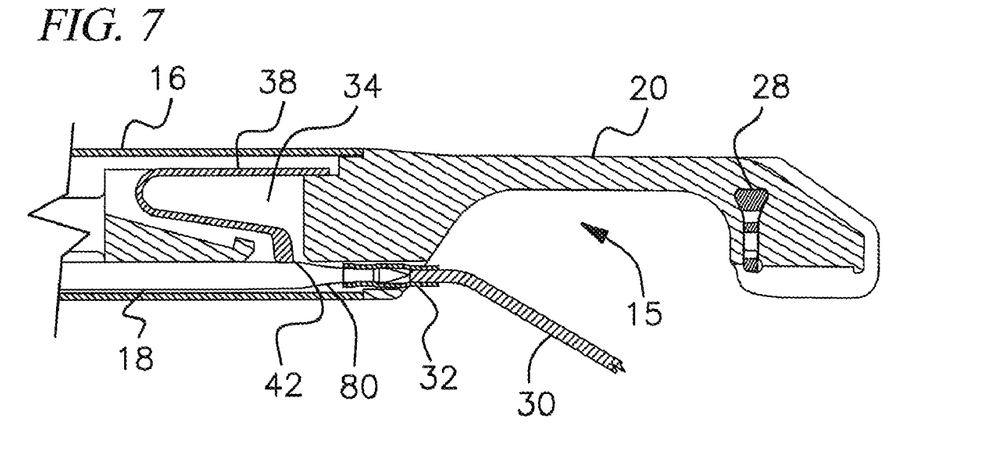
FIGS. 7-9 are sectional views corresponding to FIGS. 4-6.
Figure 8:
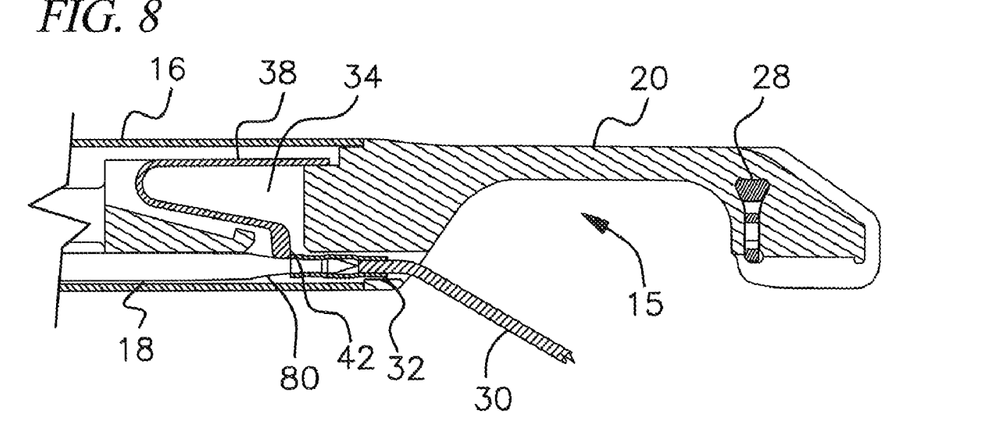
Figure 9:
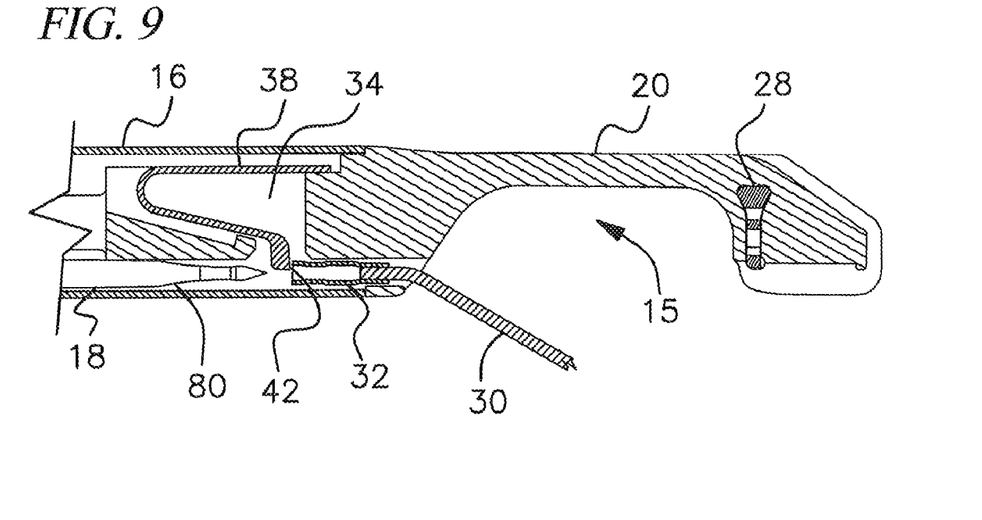

FIGS. 7 through 9 are sectional views of the stripping action of the surgical suturing instrument in accordance with this invention corresponding to FIGS. 4 through 6. FIG. 7 shows the needle 18 at the rest position with the tip 42 of the ferrule stripping spring 38 engaging the outside diameter of the needle 18, but not yet contacting the ferrule.

FIG. 8 shows the needle 18 retracted to the point where the ferrule stripping spring lip 42 initially engages the proximal edge of the ferrule 32.

FIG. 9 shows the needle 18 retracted fully and disengaged from the ferrule which was pushed off of the needle tip by the distal edge of the stripping spring lip 42.

Figures 10A, 10B:
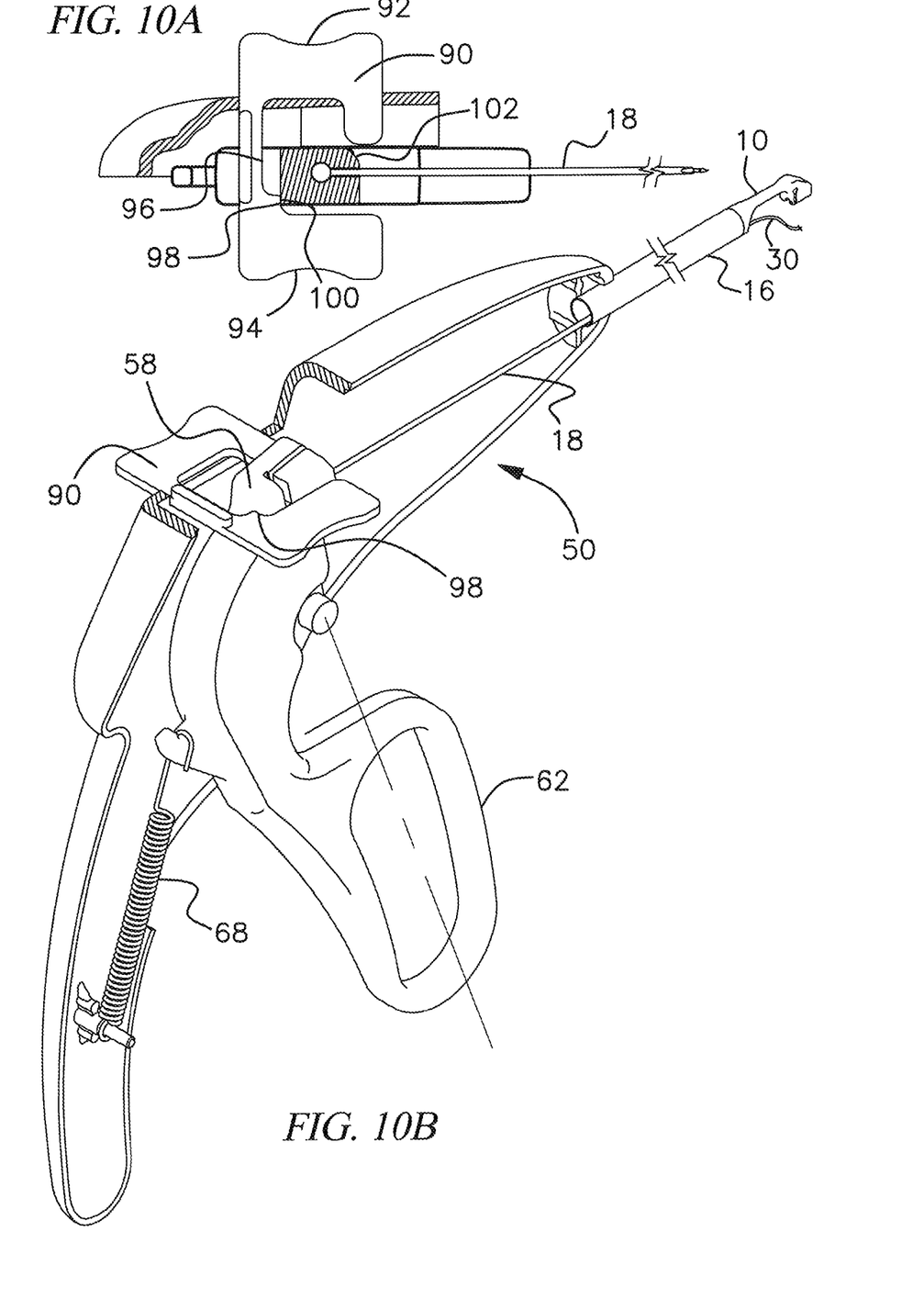
FIG. 10A is a fragmentary view, partly in section showing a latch in accordance with this invention.
FIG. 10B is a cutaway perspective view of an instrument in accordance with this invention showing a latch in accordance with an embodiment of the invention.

FIGS. 10A and B are partially cutaway views of the surgical suturing instrument 50 in accordance with another aspect of this invention. The instrument shown in FIGS. 10A and B is designed to permit the ferrule stripping operation to be performed with one hand, that is, without the need for pulling the operating lever 62 forward to strip the ferrule 32 from the tip of the reciprocating needle 18.

As shown in the figures, a slidable lever stop 90 engages the proximal portion 58 of the upper part of the actuating lever 62 when the lever is in the rest position, that is, with the needle 18 retracted to the proximal portion of the tissue receiving gap 15, but with the ferrule still in place on the tip of the needle. The slidable lever stop 90, which is generally C-shaped, has first and second curved edge portions 92, 94 adapted to be operated by the digits, or the thumb of a user, a connecting portion 96 connecting the two operating portions, and a stop 98 on the connecting portion engaging the upper portion 58 of the lever. The instrument, with the upper portion of the lever pulled back against the stop by the spring is shown in FIG. 10A. In this position, the ferrule 32 remains on the tip of the needle 18.

Figures 11A, 11B:
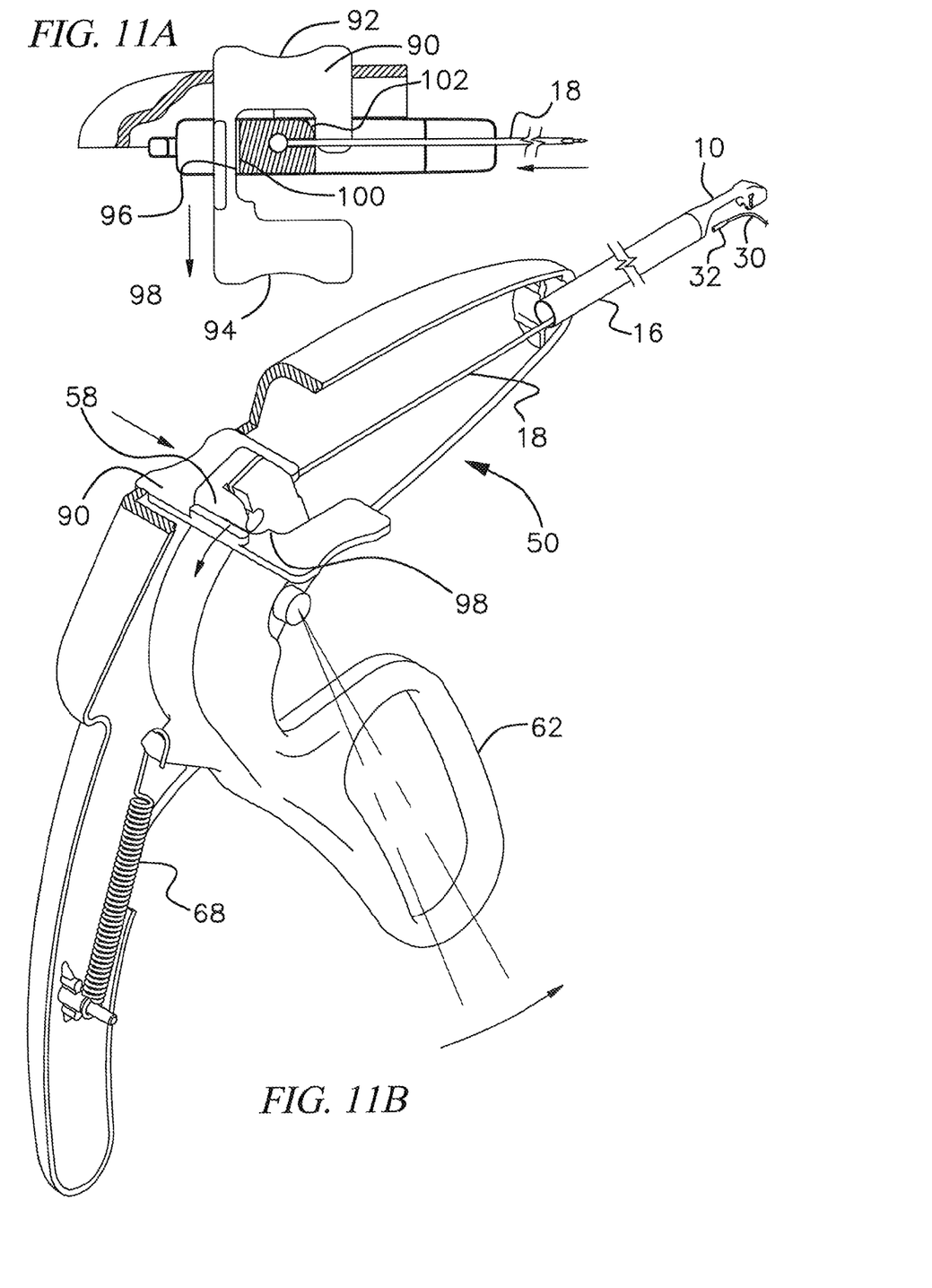
FIG. 11A is a view similar to FIG. 10A showing the latch in an engaged position.
FIG. 11B is a view similar to FIG. 10B showing the latch in an engaged position with the handle in an extended position.
Figure 12:
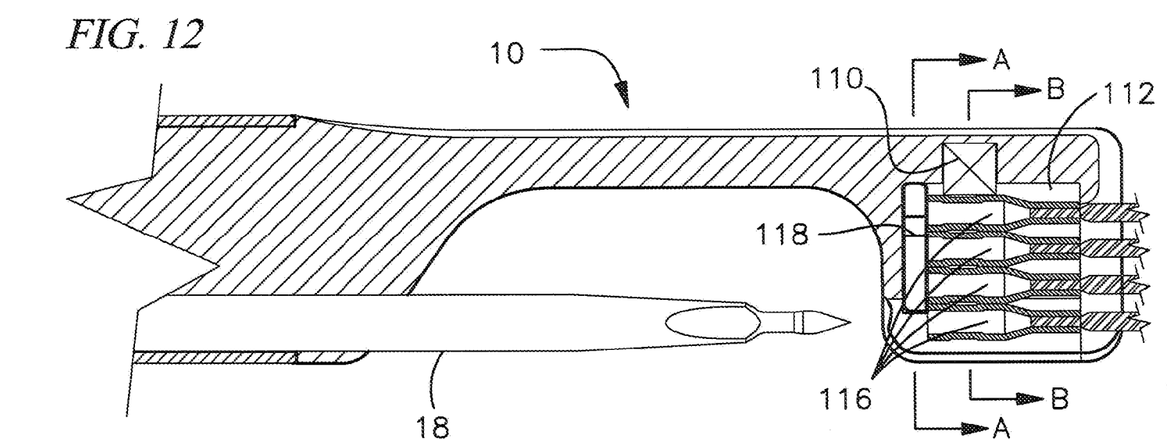
FIG. 12 is a partly sectioned view of an instrument tip showing the ferrule magazine in accordance with the invention.
Figure 13:
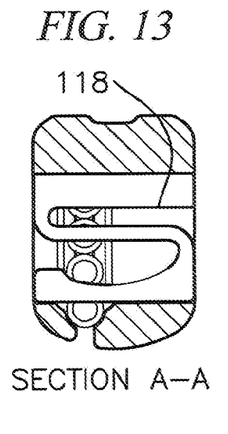
FIG. 13 is a section taken along line A-A of FIG. 12.
Figures 14, 15:
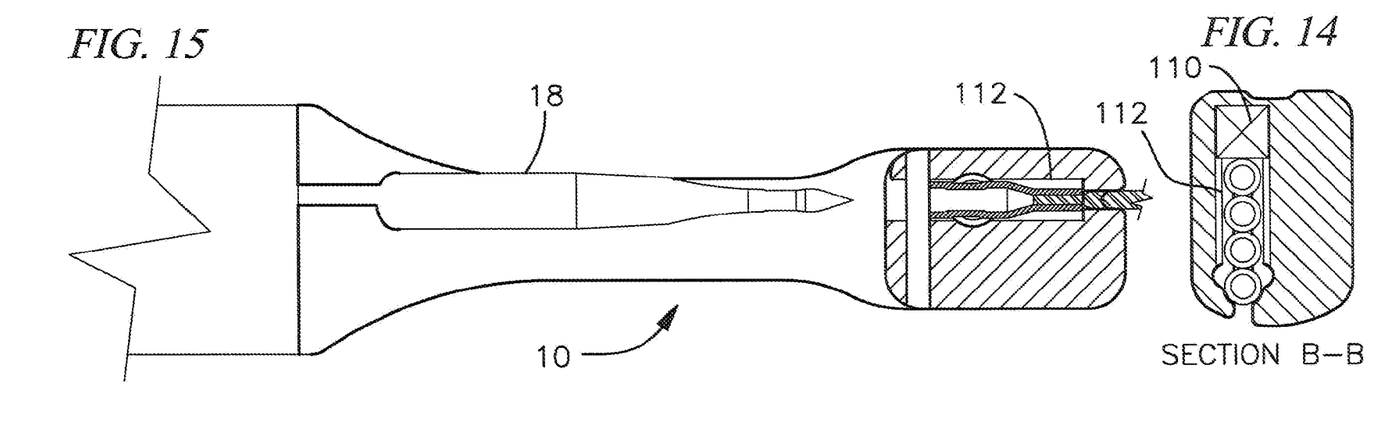
FIG. 14 is a section taken along line B-B of FIG. 12.
FIG. 15 is a bottom view of the tip shown in FIG. 12.

To strip the ferrule off the needle, the stop 90 is pushed downwardly as shown in FIG. 11A, or from left to right as shown in FIGS. 10-13 for example by pushing the curved end portion 92 with the thumb, thereby simultaneously (or at least approximately simultaneously) releasing the stop 98 from the corner 100 of the upper portion 58 of the operating lever 62 and at the same time engaging a forward portion 102 of the upper portion 58 of the operating lever to assist the spring 68 in moving the needle to a further retracted position thereby stripping the ferrule off the needle.

FIGS. 11A and 11B shows the position of the slide mechanism 90 when the needle 18 is fully retracted. To release the needle for placing a subsequent suture, the slide 90 is moved in the opposite direction, up or left as shown in FIGS. 11A and 11B, while the operating lever 62 is pulled slightly towards the handle to allow the slide to return to the position shown in FIGS. 10A and 10B.

This invention allows the reciprocating needle 18 to sequentially pick up the ends of a plurality of sutures by providing a means for stripping a ferrule from the end of the needle at the proximal edge of the tissue receiving gap 15. FIGS. 12-15 show an embodiment of the invention having a magazine formed in the distal end of the tip 10 into which a plurality of ferrules 116 can be loaded, each having a suture attached, for sequential pick-up by reciprocating motion of the needle 18. The distal end of the tip includes a magazine 112 in the form of a slot into which the plurality of ferrules 116, in this case 4, are loaded. While in this embodiment a single column of ferrules is shown, other arrangements are possible holding more. A spring 110 urges the ferrules 116 towards the bottom of the magazine slot 112 for sequential pick-up by the needle 18. A latch spring 118 as best shown in Sec. A-A, holds the ferrules 116 in place until the bottom edge of the spring 118 is displaced upwardly by the tip of the needle 18, thus releasing one ferrule at a time. Section B-B shows an end view of the ferrules 116 held by the compressed spring 110 in magazine 112.

While the invention has been described in connection with certain presently preferred embodiments thereof, those skilled in the art will recognize that certain modifications and changes may be made, therein without departing from the true spirit and scope of the invention, which accordingly is intended to be defined solely by the appended claims.

The invention claimed is:

1. A surgical suturing instrument comprising:
a housing having a handle and an actuating member;
an elongated guide member attached to the housing, and having a distal end;
a tissue engaging gap formed proximal to the distal end of the elongated guide member;
a needle extending from the housing through the guide member to the distal end, the needle reciprocally movable across the gap from a proximal end of the gap to a distal end of the gap by movement of the actuating member from a rest position to a retracted position, and movable proximally from the proximal end of the gap by movement of the actuating member to an extended position beyond the rest position in a direction opposite the retracted position.

2. The surgical suturing instrument of claim 1 comprising a ferrule stripper engaging the needle as the actuating member is moved from the rest position to the extended position.

3. The surgical suturing instrument of claim 2 in which the ferrule stripper comprises a resilient member having a ferrule engaging portion riding on the needle proximal to the tip.

4. The surgical suturing instrument of claim 2 in which the ferrule stripper engages a ferrule positioned on the needle as the actuating member is moved from the rest position to the extended position.

5. The surgical suturing instrument of claim 1 comprising a first spring biasing the actuating member from the retracted position to the rest position.

6. The surgical suturing instrument of claim 5 comprising a second spring biasing the actuating member from the extended position to the rest position.

7. The surgical suturing instrument of claim 1 in which the actuating member is pivotally mounted to the housing.

8. The surgical suturing instrument of claim 1 in which the handle is configured so it that can be gripped and the actuating member operated by one hand.

9. The surgical suturing instrument of claim 1 in which the needle has a flat surface adjacent a tip of the needle exposing a proximal edge of a ferrule when attached to the needle.

10. The surgical suturing instrument of claim 1 comprising a spring urging the handle to the extended position, and a latch stopping the actuating member at the rest position until the latch is released.

11. The surgical suturing instrument of claim 10 in which the spring comprises a slidable member having a stop movable into and out of engagement with the operating member.

12. The surgical suturing instrument of claim 11 in which the slidable member comprises a tab engaging the operating member urging it to an extended position for stripping a ferrule from the needle.

13. The surgical suturing instrument of claim 1 comprising a magazine disposed at the distal end of the gap holding a plurality of sutures.

14. The surgical suturing instrument of claim 13 comprising a latch releasing the ferrules from the magazine one at a time for pick-up by the needle.

15. The surgical suturing instrument of claim 13 in which the magazine comprises a spring biasing the ferrules to a pick-up position.

* * * * *